United States Patent [19]

Bruce et al.

[11] 4,202,858
[45] May 13, 1980

[54] MOSS KILLER

[76] Inventors: Gary Bruce, c/o George Spector 3615 Woolworth Bldg. 233 Broadway; George Spector, 3615 Woolworth Bldg. 233 Broadway, both of New York, N.Y. 10007

[21] Appl. No.: 887,874

[22] Filed: Mar. 17, 1978

[51] Int. Cl.² ........................ A61L 13/04; A61L 3/00
[52] U.S. Cl. ........................................ 422/243; 422/6; 422/29; 422/41; 422/265
[58] Field of Search ............... 422/6, 28, 29, 243, 422/265, 41; 204/147, 148, 157.1 R, 196, 197

[56] References Cited

U.S. PATENT DOCUMENTS

| | | | |
|---|---|---|---|
| 2,105,035 | 1/1938 | Krause | 422/29 X |
| 2,927,052 | 3/1960 | Moudry | 424/132 X |
| 3,479,130 | 11/1969 | Rapaport | 424/131 X |
| 3,494,727 | 2/1970 | Rapaport | 424/131 X |
| 3,598,536 | 8/1971 | Christensen | 422/265 X |

Primary Examiner—Barry S. Richman

[57] ABSTRACT

A short length of copper pipe for being dropped into a water tank, so to retard against the growth of moss in the water; and means in a modified design of the device for forcing the water to circulate through the pipe in order to increase the efficiency thereof.

2 Claims, 4 Drawing Figures

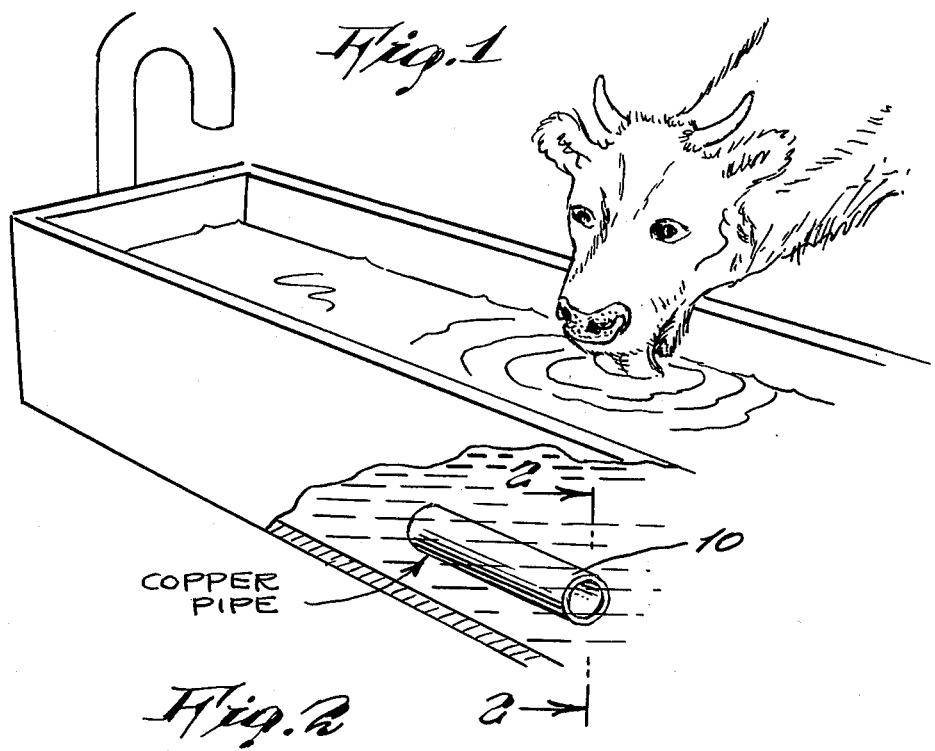
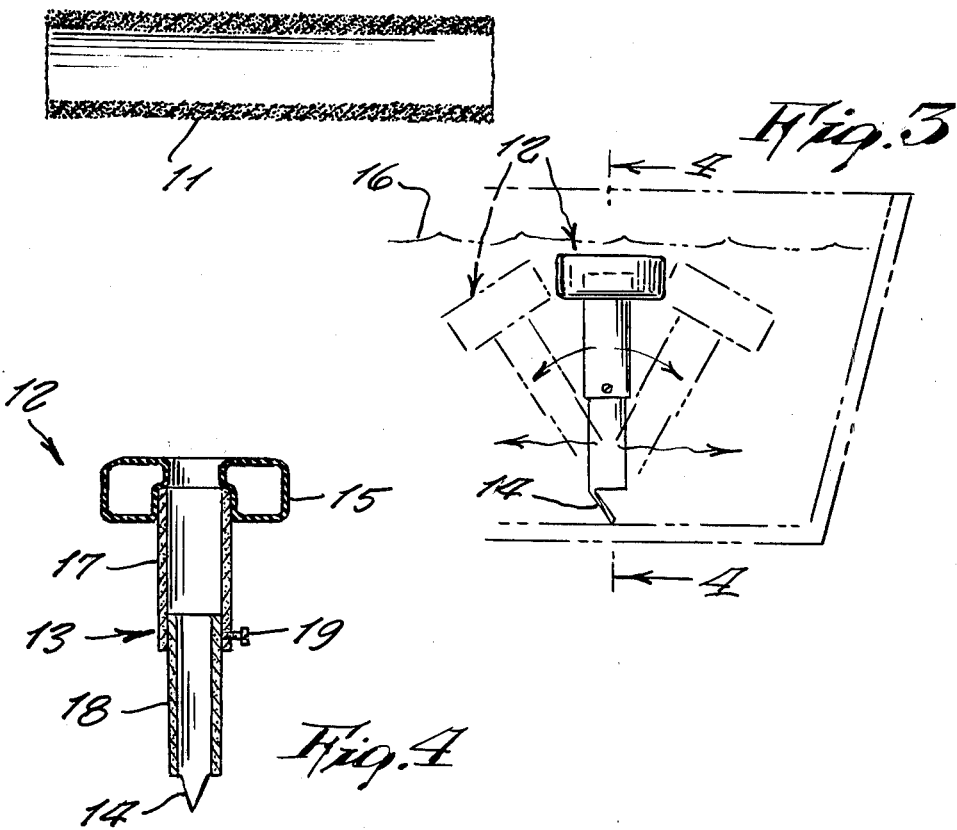

MOSS KILLER

This invention relates generally to fresh water purifying devices. More specifically it relates to plant and growth inhibitors.

A principal object of the present invention is to provide a plant growth inhibitor which can be simply dropped into a water tank so to be immediately effective in keeping the water clear of mossy growths that turn a fresh water stagnant.

Another object is to provide a plant growth inhibitor which in one design, is comprised of only a single member, so that there is no assembly work in its manufacture, nor are there moving parts that wear away.

Yet another object is to provide a plant growth inhibitor which is designed so that water can circulate therethrough in order that the water is treated more effectively thereby, the device comprising simply a short copper pipe.

Other objects are to provide a plant growth inhibitor which is simple in design, inexpensive to manufacture, rugged in construction, easy to use and efficient in operation.

These and other objects will be readily evident upon a study of the following specifications and the accompanying drawing wherein:

FIG. 1 is a perspective view showing the copper pipe invention submerged in a stock drinking trough.

FIG. 2 is an enlarged cross section on line 2—2 of FIG. 1 and illustrating a design in which the copper pipe is porous in order to have a greatly increased surface so that copper ions therefrom can disperse into the water passing therethrough.

FIG. 3 shows another design in which the copper pipe floats upright on a lower pointed end thereof, due to an inflated rubber collar around the end; this form of the invention accordingly oscillating in even a slight movement of the water (such as when an animal is drinking), so that movement of the pipe in the water increases dispersion of the copper ions; the pipe being telescopic so to fit any depth of trough.

FIG. 4 is a cross section on line 4—4 of FIG. 3, shown enlarged.

Refering now to the drawing in greater detail, and particularly to FIG. 1 thereof at this time, the reference numeral 10 represents a plant growth inhibitor which comprises simply a short length of copper pipe. It is well known that copper wire has a property that arrests marine growths, and has been used for many years as an ingredient in marine paints for the bottoms of ships so to prevent the growth of barnacles. The pipe is made of a solid copper so as to not wear away.

In operative use, it is just placed on a bottom of the tank so that the water can freely pass therethrough or around the same in order that the pipe ionizes the water.

In FIG. 1, the pipe is shown dropped in a water trough where stock such as cattle come to drink. The water is thus kept fresh and does not become stagnant from any marine growths.

In FIG. 2, another design of plant growth inhibitor 11 comprises a copper pipe that is porous instead being solid so to present a larger copper surface to the water in order to more effectively treat the water. Such pipe can be manufactureed by just pulverizing the copper into granules like sand, and thereafter being loosely placed in a mold that is then subjected to only enough heat that with weld the granules together without melting them down, so that air spaces and passages between the granules remain. Thus the passages allow movement of water therethrough afterwards.

In FIGS. 3 and 4, another design of plant growth inhibitor 12 is designed so to move or oscillate in the water in order to promote the movement of water therethrough, and is ideal for stock drinking troughs. It consists of a vertical pipe unit 13 which at its lower end is tapered to a point 14 for resting on a tank bottom and be free to rock or pivot thereupon whenever the water is moved or aggitated.

The pipe unit is maintained vertical by a floatation collar 15 at its upper end and which can be either at or below the water surface 16.

The inhibitor can be best manufactured so to readily fit the stock drinking troughs or tanks of all ranchers or farmers by being adjustable, and thus being assured that it will have a great many retail sales. Accordingly, the pipe unit is made adjustable in length to fit troughs or tanks of different water depths. The unit therefore is comprised of telescopically sliding copper pipes 17 and 18 rigidly secured together at desired length by a set screw 19. The point 14 at the lower end is made simply by being cut off to a point which is then bent to be along a concentric center axis of the pipe unit. The floatation collar comprises simply a hollow, rubber, doughnut shaped member that snap fits around the upper pipe. The pipes may be either solid or porous as above described.

It will now become readily apparent that when the inhibitor 12 is placed in a water, that it will point, oscillate or sway as shown in FIG. 3, whenever the water is disturbed by a drinking cows or by a wind blowing across the water surface, thus causing water to move past the copper pipe surfaces.

While various changes may be made in the detail construction, it is understood that such changes will be within the spirit and scope of the present invention as in defined by the appended Claims.

What is claimed is:

1. A plant growth inhibitor adapted for placement in a water container, comprising in combination a copper pipe and means for causing movement of said pipe in said water in response to water motion, wherein said means comprises a float oscillator mounted on one end of said pipe to urge said pipe to a vertical position and a tapered pivot at the opposite end of said pipe.

2. A device as in claim 1, wherein said pipe comprises adjustable telescopic sections provided with a set screw for retaining purposes.

* * * * *